(12) United States Patent
Wu (10) Patent No.: US 10,278,579 B2
(45) Date of Patent: *May 7, 2019

(54) VISION PROTECTION METHOD AND SYSTEM THEREOF

(71) Applicant: Eyes4Lives, Inc., La Habra, CA (US)

(72) Inventor: Roger Wu, West Covina, CA (US)

(73) Assignee: EYES4LIVES, INC., Tustin, CA (US)

( * ) Notice: Subject to any disclaimer, the term of this patent is extended or adjusted under 35 U.S.C. 154(b) by 373 days.

This patent is subject to a terminal disclaimer.

(21) Appl. No.: 14/300,206

(22) Filed: Jun. 9, 2014

(65) Prior Publication Data

US 2014/0285436 A1    Sep. 25, 2014

Related U.S. Application Data (63) Continuation-in-part of application No. 13/135,995, filed on Jul. 19, 2011, now Pat. No. 8,884,735, which (Continued)

(51) Int. Cl.
*A61B 3/11*      (2006.01)
*A61B 3/18*      (2006.01)
(Continued)

(52) U.S. Cl.
CPC ............... *A61B 3/18* (2013.01); *A61B 3/112* (2013.01); *A61B 3/113* (2013.01); *A61B 3/12* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 5,502,520 A | | 3/1996 | Cibis et al. |
| 6,052,119 A | * | 4/2000 | Chiang .................. G09G 5/006 345/212 |

(Continued)

OTHER PUBLICATIONS

USPTO, Authorized Officer: Copenheaver, Blaine, International Search Report for Corresponding International Application No. PCT/US2015/029122, Form PCT/ISA/220, dated Sep. 23, 2015, 4 pages.

(Continued)

*Primary Examiner* — Nabil H Syed
*Assistant Examiner* — Cal J Eustaquio
(74) *Attorney, Agent, or Firm* — William A. English; Vista IP Law Group LLP (57) ABSTRACT

A vision protection method is provided to ensure a viewer to rest his/her eyes after viewing on an electronic device for a certain period, wherein the eyesight protection method includes the steps of detecting at least one of eye activities of the viewer and working parameter of the electronic device in a working mode of the electronic device during the viewer is working on a current work displaying by the electronic device; switching the working mode of the electronic device to a resting mode when an abnormal eye activity of the viewer is detected; and switching the electronic device from the resting mode back to the working mode to resume the display of the current work of the electronic device. Therefore, the viewer is enforced to rest his/her eyes after every certain period.

18 Claims, 6 Drawing Sheets

Related U.S. Application Data is a continuation-in-part of application No. 12/313,235, filed on Nov. 17, 2008, now Pat. No. 8,884,734.

(51) Int. Cl.
| | |
|---|---|
| *G06F 3/01* | (2006.01) |
| *G06K 9/00* | (2006.01) |
| *G06Q 10/10* | (2012.01) |
| *A61B 3/113* | (2006.01) |
| *A61B 3/12* | (2006.01) |
| *A61B 3/14* | (2006.01) |
| *A61B 5/11* | (2006.01) |
| *A61B 5/00* | (2006.01) |
| *A61H 5/00* | (2006.01) |
| *A61M 21/02* | (2006.01) |
| *A61B 5/107* | (2006.01) |
| *G09G 5/00* | (2006.01) |
| *A61M 21/00* | (2006.01) |
| *A61B 5/1171* | (2016.01) |

(52) U.S. Cl.
CPC .............. *A61B 3/14* (2013.01); *A61B 5/1075* (2013.01); *A61B 5/1103* (2013.01); *A61B 5/1116* (2013.01); *A61B 5/1128* (2013.01); *A61B 5/486* (2013.01); *A61B 5/489* (2013.01); *A61H 5/00* (2013.01); *A61M 21/02* (2013.01); *G06F 3/013* (2013.01); *G06K 9/00597* (2013.01); *G06Q 10/109* (2013.01); *G09G 5/00* (2013.01); *A61B 5/1176* (2013.01); *A61B 2503/20* (2013.01); *A61B 2560/0266* (2013.01); *A61B 2560/0271* (2013.01); *A61H 2201/5007* (2013.01); *A61H 2201/5043* (2013.01); *A61H 2201/5064* (2013.01); *A61H 2201/5092* (2013.01); *A61M 2021/005* (2013.01); *A61M 2021/0027* (2013.01); *A61M 2205/056* (2013.01); *A61M 2205/3303* (2013.01); *A61M 2230/62* (2013.01); *A63F 2300/8094* (2013.01); *G06F 2203/011* (2013.01); *G09G 2354/00* (2013.01); *G09G 2356/00* (2013.01); *G09G 2360/144* (2013.01); *G09G 2360/145* (2013.01)

(56) References Cited

U.S. PATENT DOCUMENTS

| | | | |
|---|---|---|---|
| 6,210,000 B1* | 4/2001 | Yee | A61B 5/411 |
| | | | 351/83 |
| 6,421,630 B1 | 7/2002 | Yamada et al. | |
| 6,592,223 B1 | 7/2003 | Stern et al. | |
| 7,744,216 B1 | 6/2010 | Uhlhorn | |
| 9,289,125 B2 | 3/2016 | Wu | |
| 9,750,407 B2 | 9/2017 | Wu | |
| 9,901,248 B2 | 2/2018 | Wu | |
| 2001/0028309 A1* | 10/2001 | Torch | A61B 3/0066 |
| | | | 340/575 |
| 2004/0008877 A1 | 1/2004 | Leppard et al. | |
| 2004/0239517 A1* | 12/2004 | Coley | G08B 21/182 |
| | | | 340/686.6 |
| 2005/0160009 A1 | 7/2005 | Tanaka et al. | |
| 2007/0201730 A1* | 8/2007 | Masaki | G06K 9/00288 |
| | | | 382/118 |
| 2008/0100468 A1 | 5/2008 | Xu | |
| 2008/0259278 A1 | 10/2008 | Nozawa et al. | |
| 2009/0109193 A1* | 4/2009 | Masalkar | G06F 3/0425 |
| | | | 345/175 |
| 2009/0143685 A1 | 6/2009 | Elner et al. | |
| 2012/0249540 A1* | 10/2012 | Yoshino | H04N 13/341 |
| | | | 345/419 |
| 2013/0070201 A1 | 3/2013 | Shahidi et al. | |
| 2013/0235346 A1 | 9/2013 | Huang et al. | |

OTHER PUBLICATIONS

USPTO, Authorized Officer: Copenheaver, Blaine, Written Opinion for Corresponding International Application No. PCT/US2015/029122, Form PCT/ISA/237, dated Sep. 23, 2015, 9 pages.

* cited by examiner

VISION PROTECTION METHOD AND SYSTEM THEREOF

CROSS REFERENCE OF RELATED APPLICATION

This is a Continuation-In-Part application that claims the benefit of priority under 35 U.S.C. § 119 to a non-provisional application, application Ser. No. 13/135,995, filed Jul. 19, 2011, which is a Continuation-In-Part application of a non-provisional application, application Ser. No. 12/313,235, filed Nov. 17, 2008.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a method for limiting the viewing time of a viewer to protect the viewer's eyesight, and more particularly to a method of controlling an electronic device display for ensuring the viewers to rest their eyes after each predetermined period of time.

Description of Related Arts

Electronic devices are indispensable for our daily lives. People use computers for work, play video games and watch TVs during their leisure time and etc. Since many people spend a vast portion of their daily lives fixating on display screens of electronic devices, to protect a viewer's eyesight from excessive usage of any electronic device and prevent eye straining become a dramatic issue nowadays.

One of the most important factors in protection of the eyesight for electronic device viewers is to have an intermittent rest for their eyes follow a certain time of use. To protect the eyes from being over-used, the viewer should take a rest and/or do some eye exercises to help relax the muscles of the eyeballs. For example, children spend much time focusing on watching the displays of the electronic devices, such as computers for playing the ever-increasing number of games available. To compensate, the eyeball is thought to grow longer, so less effort is needed to focus up close on the computer display. When this happens, the elongated eye can no longer focus on distant objects. After the muscle of the eyeball being elongated too long, the muscle will loose its flexibility for adjusting the focus on distant objects, so that the eyesight problems such as nearsightedness and eye straining can occurred.

Even though people know how important it is to relax the eyeball muscles timely, people tend to forget taking a break and resting their eyes after viewing the display for a certain time. When people put themselves in work or indulge in a video game, it is hard to interrupt the work or video game to rest their eyes. An enforcing feature is needed to remind the viewers not to overuse their precious eyes. It is crucial that this enforcing feature can interrupt the viewer's current work, such as playing video games on an electronic gaming device, editing files on computer, or watching TV, so that the viewer won't continue to strain his or her eyes from using these devices.

A working distance between the viewer and the display of the electronic device is another important factor. Keeping certain working distance can also help to prevent the eyesight problems from getting worse quickly as well. A method or system for detecting the working distance has a great need for protecting the eyesight. Moreover, younger kids, especially those with family history of nearsightedness, tend to be more likely to develop these visual problems at an earlier age. It is becoming increasingly difficult for their parents to monitor their usage pattern on these electronic devices. Therefore, a dedicated feature on these electronic devices that can monitor both the viewers' usage and working distance is indeed necessary and crucial if we want to slow down the development of visual problems for all users.

SUMMARY OF THE PRESENT INVENTION

An object of the present invention is to provide a vision protection method and system thereof for protecting electronic device viewers from excessive usage of electronic devices and preventing eye straining.

Another object of the present invention is to provide a vision protection method and system thereof for an electronic device viewer, so that the viewer will be forced to rest his/her eyes after a certain time of usage to protect the eyes from being over-used.

Another object of the present invention is to provide a vision protection method and system thereof for protecting an electronic device viewer by ensuring the viewers to have intermittent rests of their eyes for a certain time following a predetermined period of use for the electronic device display.

Another object of the present invention is to provide a vision protection method and system thereof for electronic device viewer for an electronic device viewer, wherein the electronic device is switched from a present working mode to another temporary resting mode for a certain resting time so as to stop the viewers from viewing the display that they are working on after each predetermined time period. In which, the resting mode remains activated until the predetermined resting time is over, and that after the predetermined resting period is over, the system resumes the operation of the working mode of the electronic device that the viewer was working on previously.

Another object of the present invention is to provide a vision protection method and system thereof for electronic device viewer, wherein the display of the working mode of the electronic device that the viewer is working on is preset to be temporarily blanked out as the screen freezes or is replaced by special graphics of the resting mode.

Another object of the present invention is to provide a vision protection method and system thereof for electronic device viewer, wherein the screen displayed during the resting mode of the system is adapted for protecting the eyesight with a pattern or a photo that is soothing for the eyes.

Another object of the present invention is to provide a vision protection method and system thereof for electronic device viewer, wherein the display of the resting mode of the system can be vision therapy exercises, programs, or games designed to relax the muscles of the eyeball.

Another object of the present invention is to provide a vision protection method and system thereof for electronic device viewer, wherein the display of the resting mode of the system for protecting the eyesight is an instruction for stretching exercise, so that the viewers not only get to rest their eyes but also relax the muscles of the neck, back, arms, and wrists during these enforced break times.

Another object of the present invention is to provide a vision protection method and system thereof for electronic device viewer, wherein the system will save all information that the viewer is working on before the system switches to the resting mode to ensure that no information, files or data are lost when the working mode resumes.

Another object of the present invention is to provide a vision protection method and system thereof for electronic device viewer, which includes a setting function where the user can customize the electronic device to set up the desired working time and resting time, wherein the setting function further has a function for inputting individual information such as age, so that the resting screen of the electronic device can display the simple games or eye exercises that is suitable for each age group.

Another object of the present invention is to provide a vision protection method and system thereof, wherein a distance detector is equipped to determine the appropriate working distance between the viewer and the electronic device display. The distance detector is used in conjunction with the system to ensure that a proper distance is kept between the viewer and the display of the electronic device. And in an event that such distance is violated, a signal or a warning message will appear on the screen of the electronic device, and if the message continues to be ignored for a predetermined period of time, the electronic device will automatically switch to the resting mode.

Accordingly, in order to accomplish the above objects, the present invention provides a method for protecting the eyesight of the electronic device viewer, comprising the following steps:

initiating a time counter when a viewer starts operating an electronic device, switching the electronic device from a current working mode to a resting mode after a predetermined working time expires to force the viewer from focusing at the display of the electronic device, and switching the electronic device from the resting mode back to the working mode after a predetermined resting time expires, enabling the viewer to resume his/her previous work, wherein a loop is formed for ensuring the viewer to rest his/her eyes by providing intermittent breaks. The loop is broken only when the electronic device is shut down.

In addition, the system of the present invention is equipped with a distance detector which is a device designed to detect a working distance between the monitor and the viewer, wherein a warning message appears on the screen of the electronic device if the working distance falls below a threshold. If the viewer continues to ignore the signal or the warning message for more than a predetermined time, the system will "freeze" the electronic device immediately for another predetermined period of time before it can resume operation.

Additional advantages and features of the invention will become apparent from the description which follows, and may be realized by means of the instrumentalities and combinations particular point out in the appended claims.

Still further objects and advantages will become apparent from a consideration of the ensuing description and drawings.

These and other objectives, features, and advantages of the present invention to will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
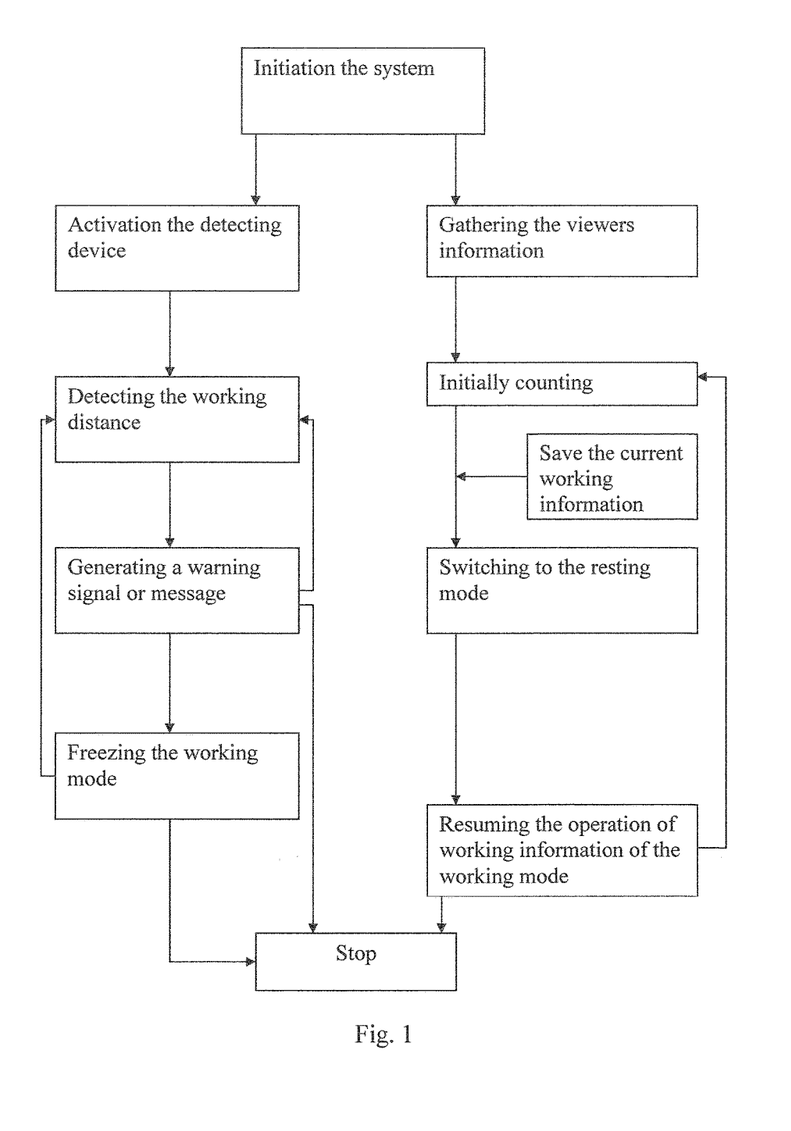
FIG. 1 is a flow chart of a method for protecting the eyesight of an electronic device viewer according to a preferred embodiment of the present invention.

Referring to FIG. 1 of the drawing, a flow chart of a method for eyesight protection of an electronic device viewer is illustrated, wherein the method includes a system comprising the following steps:

(a) initially counting down a predetermined working time in a working mode of the electronic device;

(b) switching the working mode of the electronic device to a resting mode after the predetermined working time expires for a predetermined resting time;

(c) resuming the operation of the electronic device from the resting mode back to the working mode after the predetermined resting time has elapsed; and (d) repeating the above step (a) to (c) to form a loop continuously until the viewer shuts down or halts operating the electronic device so as to ensure the viewer opportunities to rest his or her eyes after a certain period of usage.

The predetermined working time is a period of use time allowed on the electronic devices, for example, including but not limited to watching television, editing files on computer, playing video games or the likes, and the predetermined resting time is a period of time allotted for the resting mode. For example, the predetermined period of working and resting time could be pre-seted in the electronic device to one hour and ten minute respectively, so that after one hour of working on the electronic device, the electronic device will automatically switch from the working mode to the resting mode for ten minute.

In other words, the current work, such as editing files, playing games, watching television, with the electronic device will be idled by the resting mode to ensure the viewers to rest their eyes during the ten minutes resting time. The working mode of the electronic device will resume after the pre-selected ten-minute resting mode expires. The system will then re-start another one-hour countdown (the predetermined working time), and the viewer will take another ten-minute rest after that one-hour countdown expires.

The electronic device can be a computer, a cellular phone, a PDA, a notebook computer, a tablet, a hand-held gaming device, a television, a TV gaming device, and etc. When the electronic device is a programmable device such as a computer, the vision protection method of the present invention can be embodied as software, which can be purchased at a retail store or downloaded from the internet, being programmed in the electronic device to execute the above and following steps according to the present invention. The user/viewer can install it onto the electronic device with a few simple steps. The viewers can also register their names on the official website thereof and activate it by choosing the remote monitoring function on its website page without downloading or installing it to the electronic device if the viewers routinely use a public electronic device as long as that particular device has the Internet connection.

A good example of this will be computers at a public library. If a person routinely goes to a library and uses the computers there on a regular basis, he or she can still protect his/her eyesight by using this unique feature of the present invention, as long as that particular computer has an Internet connection, and the viewer does not close the window that has the eyesight/vision protection web page on. The eyesight/vision protection steps can cease running if the computer is turned off, the window with the web page is closed rather than minimized, or simply by clicking on a button on its website or pressing two or more designated keys simultaneously on the keyboard.

According to the preferred embodiment of the present invention, the resting mode is provided to temporarily freeze the current working mode for the period of resting time pre-set and ranged between 5 to 15 minutes after the predetermined working time. The users can even choose the newest 20/20/20 recommendation if so do desire (20/20/20 means after using the electronic devices for 20 minutes, the user should take a 20-second rest and look at objects that are at least 20 feet away.) After the predetermined resting time is over, the electronic device resumes from the resting mode back to the working mode so the viewers can continue doing their previous work. Accordingly, the viewers of the electronic device are ensured to have intermittent rests of their eyes for a certain time following a predetermined period of time of use of the electronic device.

During the predetermined resting time of the resting mode, the electronic device is preset or programmed to temporarily freeze the current working mode, for example temporarily blanking out the screen display of the electronic device, so as to stop the viewers from viewing the display of the electronic device that they are working on after each predetermined working time.

According to the preferred embodiment of the present invention, during the resting mode, the screen display of the electronic device may also replace the working screen with a special graphic pattern or a photo that is soothing for the eyes during the predetermined resting time for protecting the eyesight of the viewer. Alternatively, during the predetermined resting time of the rest mode, the electronic device may play relaxing music, display soothing photos, or run special programs such as some simple visual therapy games for relaxing the muscles of the eyeball.

The resting mode can also "freeze" the current work on the electronic device by "freeze-framing" on the current work, displaying a plurality soothing pictures that are relaxing for the eyes, some simple games for eye movement exercises, or an instruction for stretching exercises, so as to force the viewers to rest their eyes. In other words, the resting mode is designed to interrupt the current work of the viewer while the viewer is using the electronic device for the predetermined working time. The resting mode serves as a forceful reminder for the viewers to rest their eyes and even provides some entertaining activities or visually enhancing exercises for the viewers while they wait for the "resting time" to expire when using the electronic device.

Before switching from the working mode to the resting mode, the electronic device is programmed to automatically save the current files, data, or working information accumulated by the viewer during the working mode, so that after the resting time is expired, the electronic device resumes normal operation and the viewers can continue from where they were left off right before the resting mode was activated. With this critical feature intact, the viewers can continue their previous work after taking a short break.

The present invention further includes a step of gathering the personal information of the user (viewer) to further customize this method and system of the present invention, where during the initial set-up, the viewers or the parents of the minor viewers can enter the viewer's names, age, and select their preference, usage settings such as the desired working time and the desired resting time according to the viewer's need. It also stores multiple sets of personal information so that it can accommodate multiple viewers for the same electronic device. The viewer can also select from a list of display options during the resting mode, such as a "freeze frame" display, pictures, games, instruction for visual relaxation or instruction for stretching exercise. The age information entered during the initial set-up will be used so that during the resting mode, the method and system of the present invention will choose the appropriate games or instructions suitable for that age group.

The vision protection method of the present invention further comprises a bypassing feature with a preset password that can be entered by people such as parents for emergency reasons. For example, if it is getting really late, and the viewer's work absolutely has to be done, the resting mode can be deactivated immediately by entering the password.

Figure 2:
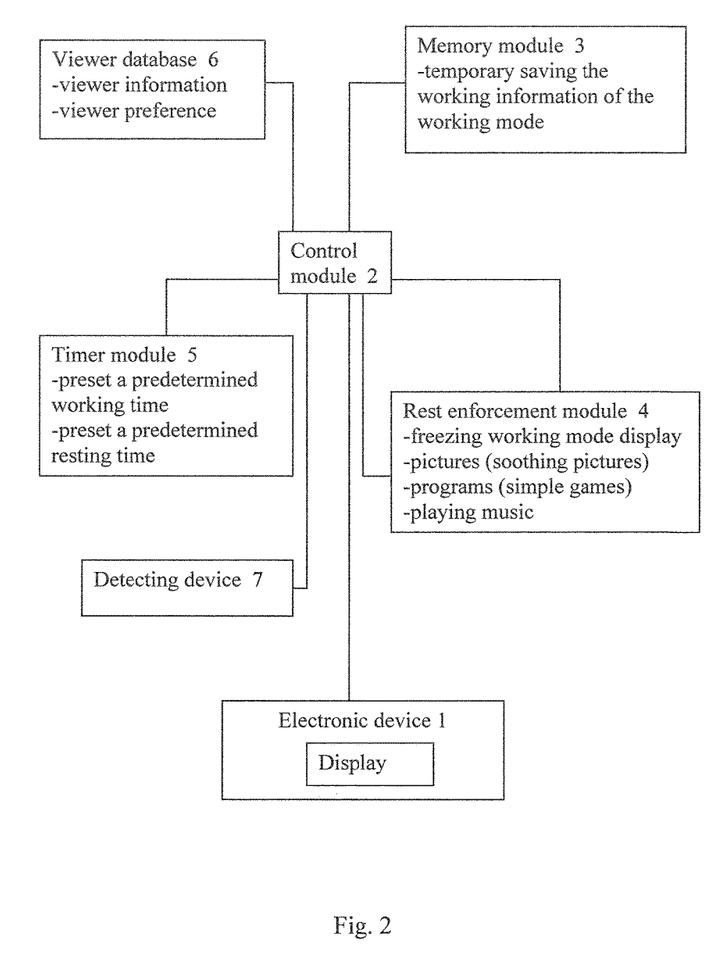
FIG. 2 is a block diagram of a vision protection system according to the preferred embodiment of the present invention.

The vision protection method of the present invention can be embodied to be performed by a system equipped with the electronic device 1 as shown in FIG. 2 of the drawings. The vision protection system for the viewer of the electronic device 1 comprises a control module 2 for coordinating the devices or modules, a memory module 3 for saving the working information, data, or files that the viewer is currently working on, a rest mode enforcement module 4 where a plurality of resting mode activities are stored, a timer module 5 that does the countdown for both the predetermined working time and resting time, and a viewer database 6 for saving the information and preference of the viewer.

According to the preferred embodiment of the present invention, the predetermined working time that ranges from 30 minutes to 1 hour and the predetermined resting time that ranges from 5 to 15 minutes, or the aforementioned 20/20/20, are saved in the timer module 5. As soon as the viewer turns on the electronic device, the timer module 5 starts counting down the predetermined working time. And when the countdown reaches zero, the timer module 5 then sends out a signal, through the control module 2, to the memory module 3, so that the memory module 3 saves all the working information, data, or files that the viewer is working on, before the system temporarily freezes the working mode and switches over to the resting mode in the rest enforcement module 4.

Once the resting mode is activated, the timer module 5 starts another new countdown for the predetermined resting time. After the predetermined resting time is over, the system then switches the electronic device from the resting mode back to the working mode and resumes all operations prior to the mandatory rest. The viewer is instructed to rest their eyes for 5 to 15 minutes after approximately every one hour of using the electronic device. The timer module 5 will repeat the countdown after switching back to the working mode, and ultimately, a loop is formed and intermittent break times are enforced.

The rest enforcement module 4 further comprises a plurality of types of display options for the resting mode, wherein these options are used to either "freeze" the current work display, or "replace" it with a totally different program designed for visual relaxation. The resting mode display can have any of the following options: a "freezing-mode" that temporarily freezes the current display of the working mode; a picture that is soothing for the eyes; a simple game designed for visual relaxation or ocular movements; an instruction for ocular exercises or an instruction for stretching exercises, and etc. . . . . .

The viewer database 6 comprises the storage of both the viewer information and the viewer preferences, wherein the database has a setting function with an input interface provided for the viewers to key in their personal information such as name, age, and select their preferences of desired working time, resting time, and activities performed during the resting mode. This customization substantially helps the system in choosing the appropriate games or pictures for the age group during the resting mode of the resting enforcement module 4. In other words, the viewer database 6 of the system is provided so that program can accommodate multiple users (viewers) for that particular electronic device 1. When the electronic device 1 is turned on, the vision protection system of the present invention is programmed to ask the viewer to select his/her name from the list of viewers already saved, so that system can upload that user's setting accordingly before the normal operation of the electronic device can begin.

It is worth mentioning that the timer module 5 automatically starts counting down the predetermined working time when the electronic device is turned on. The viewer can install the vision protection system to the electronic device 1, so that when the viewer turns on the electronic device 1, the timer module 5 automatically starts counting down the predetermined working time so as to activate the vision protecting system.

The vision protection system further comprises a detecting device 7, provided to measure the working distance between the viewer and the display of the electronic device 1, wherein when the electronic device 1 is turned on, the control module 2 activates the detecting device 7 simultaneously to determine the proper working distance. The detecting device 7 can be embodied to use a sensor such as infrared, radio wave, laser, sonar, microwave, optical sensor, optical range sensor, radar, or other alternatives to detect the working distance. The detecting device 7 may be built in or mounted on the display of the electronic device 1 and faces toward the viewer, so that if the distance measured by the detecting device 7 between the viewer and the display of the electronic device 1 falls below a predetermined range, the system will generate a warning message or signal on the screen to instruct the viewer to move back to maintain the proper working distance between the display and the viewer. Moreover, if the viewer continues to ignore this message for more than a predetermined warning time, the system will temporarily freeze the electronic device 1, and immediately switch to the resting mode before it can resume operation.

In other words, after activation of the system of the present invention, the step of gathering viewer information and the step of detecting the working distance start simultaneously. Take a 17" display of a computer screen for example, after activating the working-distance detector 7, it will monitor the actual working distance continuously to make sure that the proper distance is kept at all times. When the working distance falls below for example 45 cm, the system will generate a warning message on the display to advice the viewer to move back. If the viewer continues to ignore that message for more than 10 seconds, for example, the system will temporarily freeze the electronic device immediately for 5 minutes before it can resume operation.

The vision protection system can further be enhanced with the service and support of an eye doctor, wherein the doctor will be assigned a personal ID number, so that if the program/system is purchased directly from the viewer's eye doctor, he or she can enter that ID number during the initial set-up. In that way, a manager of the system can track and pay out the commission to the doctor accordingly, and approximately 30 days before the system expires, a reminding message will appear on the display of the electronic device every time it's turned on, not only to tell the viewer that it's time to renew the system, but also it's time to get his/her eyes examined, with the doctor's contacting information attached next to it.

As mentioned above, the vision protection system can be bypassed with a preset password that can be entered by people such as parents for emergency reasons. For example, if a child needs to finish his/her homework and it is getting really late at night, the parent can simply choose to bypass the system by entering the password. Another example will be two people taking turns using the electronic device. The viewers can bypass the resting mode with the password, so that they can skip the unnecessary resting time.

It is also important to mention that the eyesight/vision protection system will have a default setting for rest enforcement module 4, timer module 5, and detecting device 7. These default settings are designed as the safety net in cases where viewers fail to set up the program/system properly or if they are uncertain about the ideal working time, resting time, or working distance for them.

Figure 3:
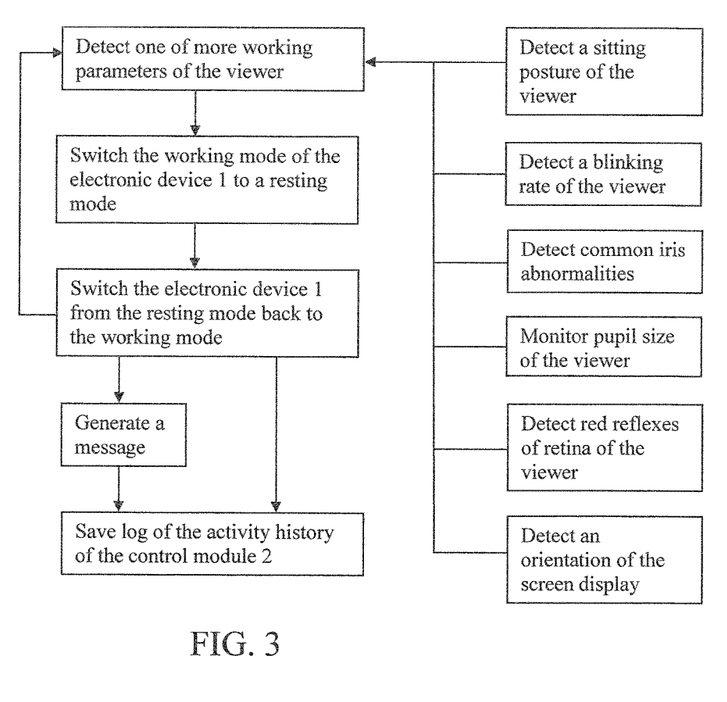
FIG. 3 is a flow chart of a method for protecting the eyesight of an electronic device viewer according to the preferred embodiment of the present invention, illustrating a modification of the method.

As shown in FIG. 3, the present invention further provides a modification of a method for eyesight protection of an electronic device viewer, which comprises the following steps.

(1) Detect one of more working parameters of the viewer in responsive to a preset working threshold in a working mode of the electronic device 1 during the viewer is working on a current work displaying by the electronic device 1.

(2) Switch the working mode of the electronic device 1 to a resting mode when the working parameter is over the working threshold for protecting the viewer from excessive usage of the electronic device 1 by halting a screen display of the current work so as to ensure the viewer to rest eyes thereof for a predetermined resting time.

(3) Switch the electronic device 1 from the resting mode back to the working mode to resume the display of the current work of the electronic device 1 after the predetermined resting time has elapsed.

(4) Repeat the above steps (1) to (3) to form a loop continuously until the viewer terminates operating the electronic device 1 so as to ensure the viewer opportunities to have intermittent rests of eyes thereof after each of the predetermined working times.

Figure 4:
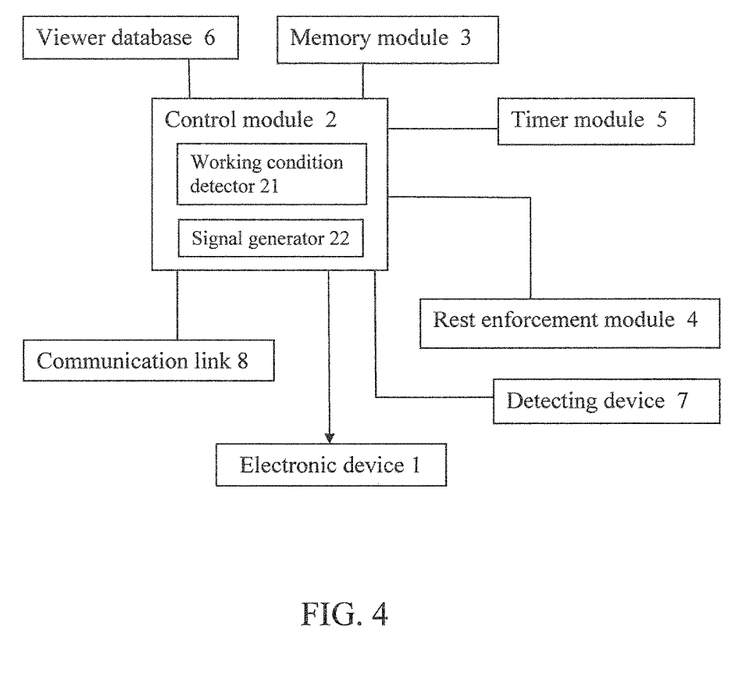
FIG. 4 is a block diagram of the modified vision protection system according to the preferred embodiment of the present invention.

As it is mentioned above, the vision protection method of the present invention can be embodied to be performed by a system equipped with the electronic device 1. The vision protection system for the viewer of the electronic device 1 comprises a control module 2 for coordinating the devices or modules, a memory module 3 for saving the working information, data, or files that the viewer is currently working on, a rest mode enforcement module 4 where a plurality of resting mode activities are stored, a timer module 5 that does the countdown for both the predetermined working time and resting time, and a viewer database 6 for saving the information and preference of the viewer.

The control module 2 has a preset working threshold and comprises a working condition detector 21 for detecting one of more working parameters of the viewer in a working mode of the electronic device 1 during the viewer is working on a current work displaying by the electronic device 1. Accordingly, the working condition detector 21 can be the detecting device 7 as mentioned above to measure the working distance between the viewer and the display of the electronic device 1.

In addition, the control module 2 further comprises a signal generator 22 operatively linked to the rest mode enforcement module 4 for generating a message on the screen display when the electronic device 1 is switched to the resting mode.

In this modification, the working condition detector 21 comprises an image capturer operatively linked to the rest mode enforcement module 4 for detecting a working condition of the viewer including sitting posture of the viewer, blinking rate of the viewer, common iris abnormalities, pupil size of the viewer, red reflexes of retina of the viewer, and orientation of the screen display. In particular, the image capturer of the working condition detector 21 comprises a high-resolution camera with facial recognition module adapted for being installed into the electronic device 1 for detecting the working condition of the viewer. The high-resolution camera can be mounted onto the screen display or built-in with the screen display for capturing an image of the viewer in front of the screen display. The facial recognition module can be embodied as software being installed into the electronic device 1 in order to operatively link with the high-resolution camera.

In the step (1), the working condition detector 21 is arranged for detecting a sitting posture of the viewer as one of the working parameters of the viewer, wherein when an improper sitting height of the viewer is detected, the electronic device 1 is switched from the working mode to the resting mode. Accordingly, the working condition detector 21 will monitor the sitting position of the viewer that if improper sitting height is detected, correction will be required to ensure proper usage of the screen display. In this situation, the signal generator 22 will generate a sitting posture message on the screen display for notifying the viewer to correct the sitting posture.

The working condition detector 21 is also arranged for monitoring a blinking rate of the viewer as one of the working parameters of the viewer. Accordingly, when the blinking rate of the viewer is below the working threshold, the electronic device 1 is switched from the working mode to the resting mode. Since the blinking rate decreases as the eyes are fixating on an object, such as the screen display, it is a major cause of electronic device-related dry eye problems. The control module 2 will count each blink and if the rate fails dangerously low, the signal generator 22 will provide a warning message.

The working condition detector 21 is also arranged for capturing the common iris abnormalities as one of the working parameters of the viewer, wherein when the common iris abnormalities is detected, the signal generator 22 will generate an advising message on the screen display for advise the viewer to seek professional opinion.

The working condition detector 21 is also arranged for monitoring the pupil size of the viewer to prevent pseudo-myopia. Accordingly, the viewers, especially for younger users, can over-use the electronic device causing their tiny eye muscles (called ciliary muscles) to strain. Hence, the size of the pupil will be more constricted than usual. By detecting the unusually small pupil size of the younger users, the control module 2 can adjust the resting time accordingly.

The working condition detector 21 is also arranged for detecting the red reflexes of the healthy retina in kids. Ocular tumors such as retinoblastoma are one of the most serious causes for childhood blindness. People who suffer from it will lose the red reflexes from the retina when a light source is shined into the eyes. The camera of the working condition detector 21 with a light source will capture a baseline photo and the control module 2 will then analyze the red reflexes. If unusual red reflexes are found, the signal generator 22 will generate an advising message on the screen display that guardian or parents will be notified.

The working condition detector 21 further comprises an orientation monitor operated coupled with the screen display, wherein the orientation monitor can be a gyroscope or an oscillation monitor to ensure the viewer of the electronic device 1 is not lying down or use the device in a moving vehicle when excessive movement can potentially strain the eyes even further.

As it is mentioned above, during the resting mode, the rest mode enforcement module 4 will selectively provide one or more of the resting mode activities including:

(i) idling the electronic device 1 for the predetermined resting time, (ii) temporarily freezing the current work of the electronic device 1, (iii) temporarily blanking out the screen display of the electronic device 1 for the predetermined resting time so as to stop the viewer from viewing the display of the electronic device, (iv) replacing the screen display of the current work of the electronic device 1 with a graphic display that is soothing for the eyes of the viewer for the predetermined resting time, (v) playing relaxing audio sounds, and (vi) running a program selected from a group consisting of a visual therapy game for relaxing muscles of the eyes of the viewer, a game for eye movement exercises, and an instruction for stretching exercises. Accordingly, an iridology program will be provided for entertainment purposes.

It is worth mentioning that the resting mode activities can be pre-selected by the viewer or can be preset by the rest mode enforcement module 4 that one of the resting mode activities will be randomly activated. In addition, the current working information and data of the working mode will be automatically saved when the electronic device 1 is switched at the resting mode. Once the electronic device 1 is activated to return back to the working mode, the electronic device 1 resumes all the current working information and data and the viewer is able to continue from where the viewer was left off right before the resting mode is re-activated.

The system of the present invention may further comprises a communication link 8 operatively linked to the control module 2, wherein the control module 2 can be remotely controlled through the communication link 8. Therefore, the parents can monitor and supervise the kid as the viewer in a distance. Accordingly, the communication link 8 is preferably an Internet connection link or a phone line connection link that the signal generator 22 can link to the mobile phone of the parents through the communication link 8, such that the signal generator 22 not only generates the message on the screen display of the electronic device 1 when the electronic device 1 is switched at the resting mode, but also generates a message such as a text message to the mobile phone of the parents through the communication link 8.

In addition, the viewer database 6 can be linked to the database of the eye doctor through the communication link 8, such that the eye doctor can instantly notify any eye problem of the viewer, especially the common iris abnormalities, strabismus, and/or symptom of ocular tumors such as retinoblastoma being detected by the working condition detector 21. Accordingly, the log of the activity history of the control module 2 will be saved in the viewer database 6 for analysis purpose.

Figure 5:
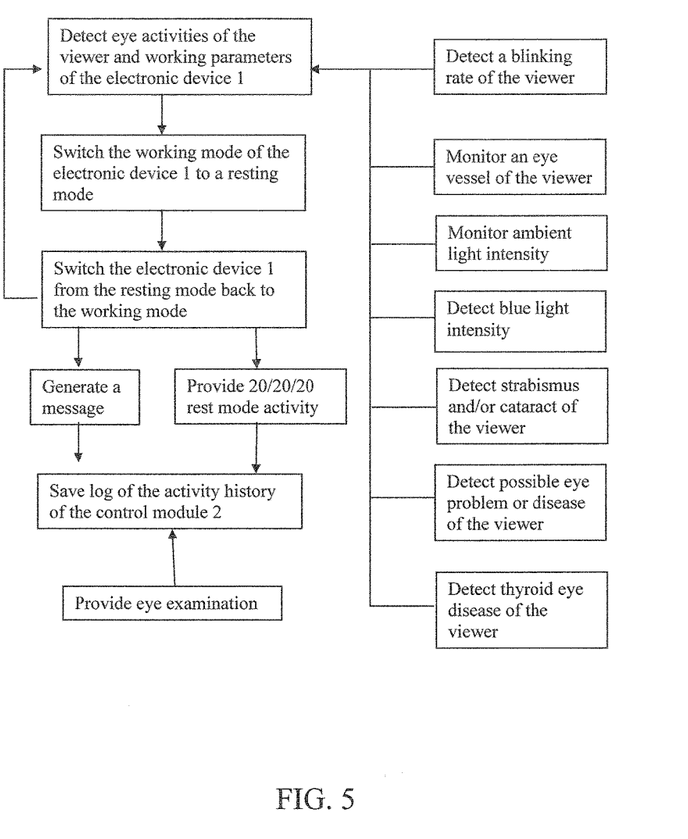
FIG. 5 is a flow chart of a method for protecting the eyesight of an electronic device viewer according to the preferred embodiment of the present invention, illustrating a second modification of the method.
Figure 6:
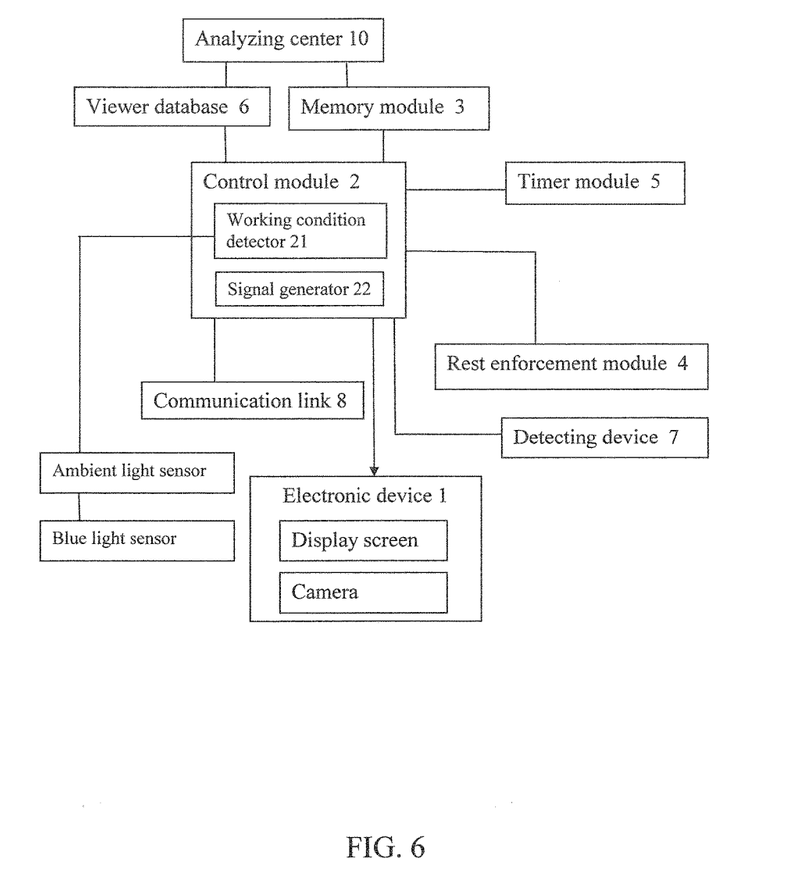
FIG. 6 is a block diagram of the second modified vision protection system according to the preferred embodiment of the present invention.

As shown in FIG. 5, the present invention provides a vision protection method and vision monitoring method for eyesight protection of a viewer of an electronic device. In other words, the present invention provides a vision care method for the viewer of the electronic device and is a modification of the above mentioned method and system. Therefore, the modification of the present invention as shown in FIGS. 5 and 6 will include all the above mentioned features and newly added features as mentioned below.

The present invention provides a vision care software to be installed in the electronic device. Preferably, the vision care software will be executed once the electronic device is switched on. The present invention may include an external camera to operatively link to the electronic device or may control the built-in camera of the electronic device via the vision care software. The present invention will detect at least one of eye activities of the viewer and working parameter of the electronic device in the working mode of the electronic device via the working condition detector 21 operatively linked thereto during the viewer is working on a current work displaying by the electronic device. When an abnormal eye activity of the viewer is detected, the working mode of the electronic device is automatically switched to the resting mode by the vision care software for protecting the viewer from excessive usage of the electronic device. In particular, the screen display of the current work is halted to ensure the viewer to rest eyes thereof for a predetermined resting time. Then, the electronic device will be automatically switched from the resting mode back to the working mode by the vision care software to resume the display of the current work of the electronic device after the predetermined resting time has elapsed. It is worth mentioning that the above mentioned loop is continuously formed until the viewer terminates operating the electronic device so as to ensure the viewer opportunities to have intermittent rests of eyes thereof after each of the predetermined working times.

As it is mentioned above, the working condition detector 21 is arranged for monitoring an eye blinking rate of the viewer as one of the ocular activities of the viewer. Accordingly, the average person tends to blink between 12 and 18 times per minute. Therefore, taking an average of 15 blinks per minute. It is worth mentioning that the viewer will blink less than 12 times per minute when the viewer stares at the screen display of the electronic device 1.

In order to determine the number of eye blink of the viewer, the working condition detector 21 will determine the sclera of the viewer. Accordingly, sclera is known as the white of the eye and is opaque. The high-resolution camera of the working condition detector 21 will continuously capture the eye image of the viewer. When the eye of the viewer opens, each eye image captured by the working condition detector 21 will show the white pixel and non-white pixel. The white pixel of the eye image is the image of the sclera of the viewer while the non-white pixel of the eye image is the iris of the viewer. When the viewer blinks his or her eye, the sclera of the viewer is covered by the eyelid. Therefore, when the eye image captured by the working condition detector 21 does not show any white pixel, the working condition detector 21 will determine the eye blink of the viewer. After a predetermined capturing time with a known capturing rate, such as ten eye images per second, the working condition detector 21 will determine how many eye images not having the white pixel so as to determine how many times the viewer blinks. In other words, once the white pixel is interrupted, the working condition detector 21 will count the viewer blinking one time. It is worth mentioning that the working condition detector 21 will focus on one of the eyes of the viewer only because both eyes of the viewer will blink at the same time. It is worth mentioning that the camera can be an external camera operatively linked to the working condition detector 21 or can be the built-in camera of the electronic device 1 to be controlled by the working condition detector 21.

When the blinking rate of the viewer is detected below the blinking threshold, the electronic device 1 is switched from the working mode to the resting mode. Since the blinking rate decreases as the eyes are fixating on an object, such as the screen display, it is a major cause of electronic device-related dry eye problems. The control module 2 will count each blink and if the rate fails dangerously low, the signal generator 22 will provide a warning message.

The working condition detector 21 is also arranged for monitoring a conjunctival blood vessel of the viewer as one of the ocular activities of the viewer. The high-resolution camera of the working condition detector 21 will continuously capture the image of the viewer's eyes to determine the conjunctival blood vessel thereof. If more than one conjunctival blood vessel is found, the working condition detector 21 will locate the blood vessel having the biggest diameter in the eye image as a reference. Accordingly, the working condition detector 21 will frequently capture the eye image to compare the caliber/diameter of the same blood vessel of the eye in the initial eye image with the same blood vessel of the eye in the latest eye image. For example, the working condition detector 21 will capture the eye image 30 minutes to one hour after the first eye image is captured. If the blood vessel of the eye is getting thicker, the working condition detector 21 will determine the percentage change of the diameter of the blood vessel of the eye. When the percentage change of the diameter of the blood vessel of the eye of the viewer is above the working threshold, the electronic device 1 is switched from the working mode to the resting mode. Since the conjunctival blood vessel of the eye engorges as the eyes get irritated while fixating on an object, such as the screen display, it is a major indicator of electronic device-induced dry eye problems. The signal generator 22 will provide a warning message once the percentage change of the blood vessel of the eye is larger than the predetermined diameter change threshold. Accordingly, when the working condition detector 21 captures more blood vessels of the eye of the viewer than the previous eye image, the signal generator 22 will also provide a warning message. In other words, the working condition detector 21 not only compare the diameter change of the conjunctival blood vessels but also determine the increasing number of the blood vessesl via two consequent eye images.

Furthermore, the working condition detector 21 is also arranged for monitoring the ambient light intensity as one of the working parameters for the viewer. Accordingly, the working condition detector 21 comprises an ambient light sensor operatively linked to the electronic device to detect the ambient light intensity. When the ambient light intensity is detected below a preset ambient light threshold, the signal generator 22 will generate an advising message on the screen display that guardian or parents will be notified, and the electronic device 1 is switched from the working mode to the resting mode. The signal generator 22 will also provide a warning message after a predetermined time period after the ambient light intensity is detected and is below the preset threshold. It is worth mentioning that the electronic device 1 will be resumed back to the working mode when the ambient light intensity is detected above the ambient light threshold.

In particular, the working condition detector 21 is also arranged for detecting blue light intensity as one of the working parameters for the viewer. Accordingly, blue light is produced by LED/LCD display screen as the backlight thereof, wherein blue light does have adverse ocular health effects. As the blue color wavelength is close to the wavelength of UV light, it is perceived being as dangerous to the natural lens and the retina as UV light. In particular, the blue light stimulates the blue sensitive cells in the retina. It is worth mentioning that the coatings inside a fluorescent light can produce less blue light. Even though LED/LCD lights are more efficient than the fluorescent lights, the LED/LCD light will produce a huge amount of light in the blue spectrum.

The working condition detector 21 comprises a blue light sensor operatively linked to the electronic device to detect the blue light intensity. When the blue light intensity is detected above a preset blue light threshold for a predetermined time period, the electronic device 1 is switched to the resting mode and the signal generator 22 will generate an advising message on the screen display that guardian or parents will be notified. The signal generator 22 will also provide a warning message after a predetermined time period when the blue light intensity is detected above the preset threshold. The signal generator 22 will generate the advising message and/or warning message after a period of continuous use of the electronic device.

Preferably, the blue light sensor is built-in with the electronic device to directly determine the blue light generated by the LCD/LED display screen of the electronic device. It is worth mentioning that the manufacturer of the electronic device contains a specification of the LCD/LED display screen which includes the blue light intensity. Therefore, the working condition detector 21 can directly obtain the data of blue light intensity to control the time usage of the electronic device. Since different electronic devices will generate different blue light intensities, the resting enforcement module 4 will be activated in different time periods in response to the LCD/LED display screens of different electronic devices.

The working condition detector 21 is also arranged for detecting the strabismus of the viewer as one of the eye activities of the viewer. Accordingly, strabismus is a condition in which the eyes of the viewer are not properly aligned with each other. It involves a lack of coordination between the extraocular muscles. A constant unilateral strabismus causing constant suppression is a risk for amblyopia in viewer. In order to determine the strabismus of the viewer, the working condition detector 21 will determine the corneal light reflex of the viewer. The camera of the working condition detector 21 will capture the eye image of the viewer to determine the corneal light reflexes of the left and right eyes of the viewer. Then, the working condition detector 21 will compare the relative locations of corneal light reflexes of the left and right eyes of the viewer with respect to the pupils and/or sclera thereof. If the corneal light reflexes of the left and right eyes of the viewer are not aligned properly, a suspected strabismus will be determined. (Medically, this is called Hirschberg Test.) As a result, and the electronic device 1 can switched to the resting mode and the signal generator 22 will generate the advising message and/or warning message. Also, doctor recommendation will be given according to the suspected strabismus.

The working condition detector 21 is also arranged for detecting the cataract of the viewer as one of the working parameters of the viewer, wherein when a suspected cataract is determined, the electronic device 1 is switched to the resting mode. The lenses of eyes of the viewer are shown in the eye image. Accordingly, cataract is a clouding of the lens inside the eye which leads to a decrease in vision and is the most common cause of blindness. In particular, visual loss occurs because opacification of the lens obstructs light from passing and being focused onto the retina of the eye. The camera of the working condition detector 21 will capture the eye image of the viewer via the red reflex to determine the cataract of the viewer. The working condition detector 21 will determine color change of each of the lenses of the eyes of the viewer in the eye image to detect whether the suspected cataract is found. In particular, the working condition detector 21 will generate a light via a light generator, such as a LED flashlight, such that when the viewer focuses on the light, the working condition detector 21 will capture the red reflex in the eye image of the viewer. Normally, red color will be shown in the ocular image for a normal viewer as most cataracts have a yellow hue to them. It is worth mentioning that the initial stage of cataract is determined when an orangey (red+yellow) color is shown in the ocular image of the viewer. The final stage of cataract is determined when a pale yellow color is shown in the eye image of the viewer.

The rest enforcement module 4 is configured to have a 20/20/20 rest mode activity save in the memory module 3 to guide eyes of the viewer to rest. The 20/20/20 rest mode is defined as every 20 minutes of the usage of electronic device, spend 20 seconds rest time looking at objects that are at least 20 feet away. In order to activate the 20/20/20 rest mode, the timer module 5 starts counting down twenty minutes as the electronic device is used. Once twenty minutes are up, the rest enforcement module 4 is activated. The electronic device may be idle for twenty seconds. The working condition detector 21 will detect whether the viewer looking at far objects or not by detecting the pupil size change of the viewer. In particular, the pupil size of the eye will be bigger when looking at far distance and will be smaller when looking at near object. Accordingly, working condition detector 21 will frequently capture a plurality of eye images of the viewer in the resting mode activity and compare the pupil size of the viewer in the current eye image with the pupil size of the viewer in the previous eye image.

Therefore, the working condition detector 21 will detect and compare the pupil size of the viewer when looking at the display screen with the pupil size of the viewer at the 20 seconds rest time. If the pupil size of the viewer remains unchanged or no significant change during the 20 seconds rest time, the signal generator 22 will generate the advising message and/or warning message. After 20 seconds rest time, the electronic device will resume back to working mode.

The present invention further provides a preliminary visual acuity examination pertaining to the eyes of the viewer. Accordingly, the signal generator 22 will generate the advising message to determine the distance between the eyes of the viewer and the display screen. Likewise, the detecting device 7 will measure the working distance between the eyes of the viewer and the display screen of the electronic device to ensure the proper eye examination distance. The control module 2 will display a visual acuity examination image on the display screen of the electronic device for visual acuity testing. For example, a Snellen chart is shown on the display screen of the electronic device for visual acuity testing. The eye examination result will be displayed on the display screen of the electronic device 1 and saved in the memory module 3. Since the viewer database 6 is linked to the database of the eye doctor through the communication link 8, the eye examination result can be instantly sent to the eye doctor to instantly notify any eye problem of the viewer. Preferably, doctor recommendation will be given based on the eye examination result of the viewer.

The present invention further provides a detection of a possible eye problem or disease. Accordingly, the working condition detector 21 is also arranged for detecting the iris defection or disease in response to aniridia, coloboma, dry eye syndrome, and/or contact lens problem. For example, the working condition detector 21 will capture the eye image of the viewer to indicate the possible contact lens problem. In other words, the working condition detector 21 will have the ability to detect any "hazing" on the contact lenses or white spots on the lenses, which are indicative of dirty or drying of the contact lenses and protein deposits. Furthermore, the working condition detector 21 is also arranged for detecting eyelash problem, such as madarosis, trichotillomania, blepharitis, and/or pediculosis, eye lid problems such as Meibomian gland dysfunction (MUD), and lens dislocation. For example, the working condition detector 21 will capture the eye image of the viewer and compare the eye image of the viewer with an eye image in a normal iris condition saved in the memory module 3. If any abnormal symptom is found, the signal generator 22 will generate the advising message and/or warning message.

Accordingly, the working condition detector 21 is also arranged for providing a spectacle lens examination for the viewer. The working condition detector 21 will capture the lens image of the spectacle to determine if there is any scratch on the lens or peeling of the lens coatings. By the light reflection, the lens image will shown the fine and/or deep scratches on the lens. The signal generator 22 will generate the advising message and/or warning message. Moreover, when the working condition detector 21 will also capture the ocular image of the viewer when wearing the spectacles. Once the working condition detector 21 detects the abnormal reflections from the spectacle lenses or squinting of the viewer's eyes, the signal generator 22 will generate the advising message and/or warning message to notify the spectacle problem for the viewer. Doctor recommendation will be given when a possible spectacle problem is found.

The working condition detector 21 is also arranged for detecting possible thyroid eye disease for the viewer. It is known that thyroid disease can cause thyroid eye disorder. Accordingly, due to the thyroid disease, swelling of the eye tissue in the eye socket can push the eyeball forward creating variable prominence or protrusion of one or both eyes, i.e. known as proptosis. Proptosis can stretch and/or compress the optic nerve potentially causing blurred vision, impaired color vision and permanent vision loss. The swelling may affect the muscles around the eyeball resulting in decreased ability to freely move the eye in different directions. It can cause eye fatigue, eye soreness and most notably double vision. Accordingly, by incorporating with a 3D camera, the working condition detector 21 will capture the eye image of the viewer compare the eye image of the viewer with an eye image in a normal eyeball condition saved in the memory module 3. If any abnormal symptom is found, the signal generator 22 will generate the advising message and/or warning message.

According to the preferred embodiment, the viewer database 6 and the memory module 3 can be saved in a remote network, such as "cloud server" to compute and save all the viewer information and data so as to minimize the storage space of electronic device to store the related viewer information and date. Therefore, the remote network can be controlled to serve thousands of different viewers to provide an eye care system therefor. An analyzing center 10 can be provided in the electronic device and/or the remote network to analyze the data of the viewer in the working mode and resting mode and the eye activities thereof, such that the viewer and/or the doctor can review and analyze the condition of the viewer.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A vision care method for eyesight protection of a viewer of a computer including a display, a detector oriented towards a viewer in front of the display, the detector comprising a camera communicating with a facial recognition module, and a control module coupled to the detector and the display, the method comprising:
   (a) detecting, by the control module, a viewer in front of the display using the detector;
   (b) initiating, by the control module, a working mode wherein the display presents working information to the viewer, the control module triggers a timer counting down a predetermined working time period for the working mode, and the control module monitors:
   i) a sitting posture of the viewer; and
   ii) an eye blinking rate of the viewer via images from the camera analyzed by the facial recognition module;
   (c) during the working mode, when the eye blinking rate of the viewer falls below a blinking threshold or an improper sitting height of the viewer is detected by the control module, presenting a warning on the display;

(d) after the predetermined working time has lapsed, switching the working mode of the computer to a resting mode for protecting the viewer from excessive usage of the computer by interrupting display of working information on the display so as to ensure the viewer to rest eyes thereof for a predetermined resting time;

(e) switching the computer from the resting mode back to the working mode to resume the display of working information on the display after the predetermined resting time has elapsed; and (f) repeating the above steps (b) to (e) to form a loop continuously until the viewer terminates operating the computer so as to ensure the viewer opportunities to have intermittent rests of eyes thereof.

2. The method, as recited in claim 1, wherein the eye blinking rate is detected by:

capturing a plurality of eye images of the viewer in the working mode from the camera;

determining, by the facial recognition module, whether the sclera and/or corneal light reflex of the viewer is shown in the eye images; and when the sclera and/or corneal light reflex of the viewer is not shown in the eye images, counting viewer blinks.

3. The method, as recited in claim 2, wherein the detector monitors only one eye of the viewer.

4. The method of claim 1, further comprising:

detecting a working distance of the viewer from the display to ensure that a proper distance is kept between the viewer and the display; and when the working distance falls outside a predetermined threshold, presenting a warning on the display.

5. The method of claim 1, wherein, during the working mode, the method further comprises:

detecting a working distance of the viewer from the display to ensure that a proper distance is kept between the viewer and the display; and when the working distance falls outside a predetermined threshold, presenting a warning on the display.

6. A method for eyesight protection of a viewer of a computer including a display, a detector comprising a camera oriented towards a viewer in front of the display and communicating with a facial recognition module, and a control module coupled to the detector and the display, the method comprising:

(a) detecting, by the control module, a viewer in front of the display;

(b) initiating, by the control module, a working mode wherein:

i) the display presents working information to the viewer;

ii) the control module triggers a timer counting down a predetermined working time period for the working mode; and iii) the control module monitors a plurality of parameters of the viewer using the camera and the facial recognition module, the parameters comprising:

1) monitoring a sitting height of the viewer;

2) monitoring a working distance of the viewer from the display; and 3) monitoring a blinking rate of an eye of the viewer; and iv) the control module monitors ambient light intensity using the detector;

(c) during the working mode, when the control module determines that any of the parameters or the ambient light intensity fall outside a predetermined threshold, presenting a warning on the display;

(d) after the predetermined working time has lapsed, switching the working mode of the electronic device to a resting mode for protecting the viewer from excessive usage of the computer; and (e) switching the computer from the resting mode back to the working mode to resume the display of working information on the display after the predetermined resting time has elapsed.

7. The method of claim 6, wherein, when the electronic device is switched from the working mode to the resting mode, the display of working information on the display is interrupted by the control module.

8. The method of claim 6, wherein switching the working mode of the electronic device to the resting mode comprises interrupting display of working information on the display.

9. The method of claim 6, wherein switching the electronic device to the resting mode comprises one of:

i) idling the electronic device for the predetermined resting time period; and ii) freezing the display on a final image from the working mode for the predetermined resting time period.

10. The method of claim 6, further comprising repeating steps (b) to (e) to form a loop continuously until the viewer terminates operating the electronic device so as to provide the viewer opportunities to have intermittent rest of the viewer's eyes.

11. The method of claim 10, wherein steps (b) to (e) are repeated until the control module determines that:

i) the control module determines that the viewer halts operating use of the electronic device; or ii) the viewer has shut the electronic device down.

12. The method of claim 6, wherein, during the working mode, the control module monitors ambient light intensity of the electronic device, such that when the ambient light intensity is detected below a preset ambient light threshold, a warning is presented on the display.

13. The method of claim 6, wherein, during the working mode, the control module analyzes images from the camera to detect the sitting posture of the viewer, and wherein, when the control module detects an improper sitting posture of the viewer, a warning is presented on the display.

14. A system for eyesight protection of a viewer of a computer, comprising:

a display;

a detector comprising a camera mounted relative to the display for imaging a viewer in front of the display;

a facial recognition module for analyzing images from the camera;

a control module coupled to the display, the detector, and the facial recognition module to:

(a) detect a viewer in front of the display;

(b) initiate a working mode wherein:

i) the display presents working information to the viewer;

ii) the control module triggers a timer counting down a predetermined working time period for the working mode; and iii) the control module monitors a plurality of parameters of of the viewer using the camera and the facial recognition module, the parameters comprising:

1) a sitting height of the viewer;

2) a working distance of the viewer from the display; and
   3) a blinking rate of the eye of the viewer; and
   iv) the control module monitors ambient light intensity using the detector;
(c) during the working mode, if the control module determines that any of the parameters or the ambient light intensity falls outside a predetermined threshold, a warning is presented on the display;
(d) after the predetermined working time has lapsed, switch the working mode of the computer to a resting mode for protecting the viewer from excessive usage of the computer; and
(e) switch the computer from the resting mode back to the working mode to resume the display of working information on the display after the predetermined resting time has elapsed.

15. The system of claim 14, wherein the camera is built-in the electronic device along with the display.

16. The system of claim 14, wherein, the control module is further configured to interrupt display of working information on the display when the electronic device is switched from the working mode to the resting mode.

17. The system of claim 14, wherein the control module is configured to repeat steps (b) to (e) until the control module determines that the viewer halts operating use of the electronic device, or the viewer has shut the electronic device down.

18. The system of claim 14, wherein, during the working mode, when the ambient light intensity is detected below a preset ambient light threshold, a warning is presented on the display.

* * * * *